United States Patent [19]

Walsh et al.

[11] 3,991,142

[45] Nov. 9, 1976

[54] PROCESS FOR FORMING BIS(2,3-DIBROMOPROPYL) PHOSPHITE

[75] Inventors: Edward N. Walsh, New City; Milton L. Honig, New York, both of N.Y.

[73] Assignee: Stauffer Chemical Company, Westport, Conn.

[22] Filed: Feb. 10, 1975

[21] Appl. No.: 548,312

Related U.S. Application Data

[62] Division of Ser. No. 144,265, May 17, 1971, abandoned.

[52] U.S. Cl. .......................... 260/982; 260/2.5 AJ; 260/45.7 R; 260/967
[51] Int. Cl.² ...................... C07F 9/141; C08J 9/00
[58] Field of Search ..................................... 260/982

[56] References Cited
UNITED STATES PATENTS

| | | |
|---|---|---|
| 2,834,797 | 5/1958 | Chadwick .......................... 260/461 |
| 2,852,549 | 9/1958 | Coover, Jr. et al. ................ 260/461 |
| 2,860,155 | 11/1958 | Walsh ................................ 260/461 |
| 2,984,680 | 5/1961 | Walsh ................................ 260/461 |

Primary Examiner—Anton H. Sutto
Attorney, Agent, or Firm—Richard P. Fennelly

[57] ABSTRACT

There are disclosed novel fire retardant compositions comprising blends of ordinarily flammable synthetic resins and foams together with bis(2,3-dibromopropyl) phosphite. Such blends are found to display excellent flame retardant properties. Also disclosed is an improved method for the preparation of the bis(2,3-dibromopropyl) phosphite.

7 Claims, No Drawings

PROCESS FOR FORMING BIS(2,3-DIBROMOPROPYL) PHOSPHITE

This is a division of application Ser. No. 144,265 filed May 17, 1971, now abandoned.

TECHNICAL DISCLOSURE OF THE INVENTION

The present invention comprises the novel fire retardant compositions resulting from the intimate admixture of various resins and foams which are ordinarily flammable with bis(2,3-dibromopropyl) phosphite, i.e. with

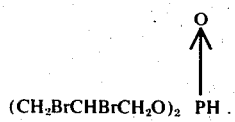

$(CH_2BrCHBrCH_2O)_2$ PH.

Thus, among the various polymeric substrates which can be rendered fire retardant upon being admixed with bis(2,3-dibromopropyl) phosphite are polymethyl methacrylate and the copolymers of methyl methacrylate with a minor proportion of one or more vinyl comonomers, urethane foams and the so-called polyester resins resulting from the condensation reaction between dibasic acids and dihydric alcohols.

The excellent flame retardant properties displayed by the compositions of this invention are believed to result from the high degree of reactivity displayed by the P-H bond of the bis(2,3-dibromopropyl) phosphite which thereby permits it to become an integral part of many of the polymeric substrates containing ethylenic unsaturation such, for example, as the maleate or acrylate double bonds found in polyesters and in methyl methacrylate polymers.

Although the preparation of bis(2,3-dibromopropyl) phosphite has been reported in the literature (see Abramov et al Khim. Org. Soedin, Fosfora Akad. Nauk SSR, Otd. Obchch. Tekh. Khim. 1967, 115), the procedure utilized is not particularly efficient. Thus, this reported procedure involves the reaction between hydrogen chloride and tris(2,3-dibromopropyl) phosphite and does not conserve all of the dibromopropyl units which are available for the reaction since many are lost via side reactions which yield non-reactive volatile products such as 1,2-dibromo-3-chloropropane.

Accordingly, a new and highly efficient method for preparing bis(2,3-dibromopropyl phosphite) has now been found which succeeds in conserving all of the available dibromopropyl units in the tris(2,3-dibromopropyl)phosphite intermediate. This new synthetic route involves the reaction between phosphorous acid, i.e. $H_3PO_3$, and tris(2,3-dibromopropyl) phosphite according to the following reaction scheme.

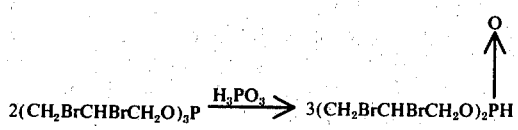

$2(CH_2BrCHBrCH_2O)_3P \xrightarrow{H_3PO_3} 3(CH_2BrCHBrCH_2O)_2PH$

In preparing the tris(2,3-dibromopropyl) phosphite intermediate which is employed in the novel process of this invention, phosphorus trichloride is reacted with three times its concentration, on a molar basis, of 2,3-dibromopropanol which has first been dissolved in a hydrocarbon solvent such, for example, as benzene, toluene, methylene chloride or chloroform with the use of benzene being preferred. This phosphorus trichloride is added over about a one hour period while a steady stream of dry nitrogen is bubbled through the solution in order to eliminate byproduct hydrogen chloride as it is formed. The reaction is conducted at a temperature of from about 0° to 5° C. since the use of higher temperatures causes undesirable side reactions. Upon completing the addition of the phosphorus trichloride, the reaction mixture is stirred for about 2 hours at 0°-5° C. while still bubbling nitrogen through the system. The desired tris(2,3-dibromopropyl) phosphite intermediate is then obtained by stripping off the solvent. The preparation of this compound is reported in French Pat. No. 1,433,208 to Albright & Wilson.

In carrying out the novel process of this invention, phosphoric acid is reacted with double its concentration, on a molar basis, of the tris(2,3-dibromopropyl) phosphite intermediate. This reaction is conducted over about a 1 to 6 hour period at a temperature of from about 80° to 150° C. with the use of a temperature of about 100° C. being preferred. Care should, however, be taken when running the reaction at temperatures near the upper end of the latter range in order to minimize decomposition of dibromopropyl units. This reaction is carried out in the presence of an inert gas such as nitrogen.

Upon completing the reaction, the reaction product is cooled down to ambient temperatures and is then taken up in a hydrocarbon, or chlorinated hydrocarbon solvent such, for example, as methylene chloride. The product is then washed with a dilute aqueous solution of an alkaline material such, for example, as sodium bicarbonate. Next, the organic layer is washed with water, separated, dried over a suitable drying material such as anhydrous magnesium sulfate whereupon the solvent is stripped. This procedure provides the desired bis(2,3-dibromopropyl) phosphite as a clear white liquid in yields which are in excess of about 85% based on the dibromopropanol used in preparing the tris(2,3-dibromopropyl) phosphite intermediate.

As has been noted, bis(2,3-dibromopropyl) phosphite provides excellent flame retardant properties upon being intimately admixed with a large number of polymeric substrates which are ordinarily highly flammable. Thus, this compound may be used to prepare flame retardant polyester resin compositions. The latter class of resins generally comprise the products made by heating a mixture of glycols, e.g. propylene or diethylene glycol, unsaturated dibasic acids or anhydrides, e.g. fumaric acid or maleic anhydride, and, optionally, a saturated dibasic acid or anhydride, e.g. isophthalic acid or phthalic anhydride and chlorodic anhydride or acid, which serves to control the reaction and modify the properties of the resulting product. To the thus prepared fluid polyester, a reactive monomer, e.g. styrene, diallyl phthalate, diallyl isophthalate or triallyl cyanurate, is then usually added and a peroxide catalyst, e.g. benzoyl peroxide, is introduced in order to catalyze the final copolymerization reaction. These polyesters, or unsaturated polyesters as they are often referred to, are thermosetting and are widely used in reinforced plastics and in the potting of electrical components.

Bis(2,3-dibromopropyl) phosphite can also be used to flame retard urethane resins which may be rigid, flexible or foamed. These polymers are ordinarily prepared by means of the reaction between an isocyanate, such as toluene diisocyanate or diphenylmethane-4-4'diisocyanate, and a second reagent comprising a polyer which contains two or more hydroxyl groups. As used in this specification, the term "isocyanate material" is intended to include any polyisocyanate or urethane compounds containing two or more unreacted —NCO radicals. The most common urethane resins are formed by reaction of toluene diisocyanate and a polyether or polyester polyol. Representative polyesters are the reaction products of adipic acid and/or phthalic anhydride and ethylene glycol. Other polyols which may be used in place of the polyesters are polyethers, such as the polyoxypropylenediols and polyoxypropylene triols, castor oil, methyl glucoside polyether polyols and drying oils, etc.

Urethane foams differ from other cellular plastics in that the chemical reactions causing foaming occur simultaneously with the polymer-forming reactions. As in the case of urethane resins, the polymeric constituent of urethane foams is made by reacting a polyol with an isocyanate. When the isocyanate is in excess of the amount that will react with the polyol, and when water is present, the excess isocyanate will react with water to produce carbon dioxide which expands the mixture. Urethane foams may be flexible or rigid and may have open or closed cells, depending largely on the polyol used. Crosslinked foams are rigid or semi-rigid. Auxiliary blowing or foaming agents, such as the various halohydrocarbons, are sometimes used, especially in rigid foams. Other ingredients often incorporated in urethane foams are catalysts to control the speed of reaction, and a surfactant to stabilize the rising foam and control cell size.

Three basic processes are used for making urethane foams: the prepolymer technique, the semi-prepolymer technique and the one-shot process. In the prepolymer technique, a polyol and an isocyanate are reacted to produce a compound which may be stored and subsequently mixed with water, catalyst and, in some cases, a foam stabilizer. In the semi-prepolymer process, about 20% of the polyol is prereacted with all of the isocyanate and this product is later reacted with a masterbatch containing the remainder of the ingredients. And, in the one-shot process, an isocyanate, a polyol and catalyst are fed into separate streams to a mixing head from which the mixed reactants are discharged into a mold.

Regardless of the procedure utilized for their preparation, polyurethane foams are enjoying ever increasing utilization in a wide variety of applications including their use in household appliances, airplane construction, padding for mattresses and upholstery, interlinings for overcoats and sleeping bags, soundproof walls, insulation against heat loss, life preservers, fish net floats, foam rubber specialties, air filters, packaging and bone surgery.

Another class of polymeric substrates which can be rendered flame retardant by being blended with bis(2,3-dibromopropyl) phosphite are the polymers of methyl methacrylate including polymethyl methacrylate and the copolymers of methyl methacrylate with minor proportions of one or more alpha, beta-ethylenically unsaturated comonomers. Applicable comonomers include the $C_1$–$C_8$ alkyl, cycloalkyl and bicycloalkyl esters of acrylic acid and the $C_2$–$C_8$ alkyl, cycloalkyl and bicycloalkyl esters of methacrylic acid such, for example, as ethyl acrylate and methacrylate, butyl methacrylate, 2-ethylhexyl methacrylate, norbornyl acrylate, and cyclohexyl acrylate; vinyl aryl compounds such, for example, as alphamethyl styrene and styrene; and, nitriles of alpha, beta-ethylenically unsaturated carboxylic acids such, for example, as acrylonitrile and methacrylonitrile.

The above described homo- and copolymers of methyl methacrylate can be prepared by means of polymerization procedures well known to those skilled in the art. Such procedures include free radical initiated bulk, solution and emulsion techniques as well as procedures which are initiated by the use of ionic or so-called Ziegler catalysts.

Other polymeric substrates with which bis(2,3-dibromopropyl) phosphite can be admixed in order to provide flame retardant blends include but are not limited to:

Polymers of nitriles of ethylenically unsaturated acids including polymethacrylonitrile, polyacrylonitrile and the copolymers of methacrylonitrile or acrylonitrile with a minor proportion of one or more vinyl monomers such as the lower alkyl acrylates and methacrylates, styrene and alpha-methyl styrene;

Acrylonitrile-butadiene-styrene resins, commonly referred to as "ABS" resins, which generally comprise either a mixture of a 60 to 80:40 to 20 styrene:acrylonitrile copolymer with from about 10 to 40%, by weight of a 5 to 40:95 to 60 acrylonitrile-butadiene copolymer or a mixture of a 60 to 80:40 to 20 styrene:acrylonitrile copolymer with from about 10 to 40%, by weight, of a graft of the latter copolymer onto polybutadiene;

Poly(alpha-olefins) such as polypropylene and polyethylene and copolymers of one or more alpha-olefins, such as ethylene or propylene, with a minor proportion of one or more ethylenically unsaturated monomers including 4-methyl pentene-1, butene-1, norbornene and its derivatives, cyclopentadiene, cyclopentene, cyclobutene, vinyl acetate, the $C_1$–$C_{12}$ alkyl acrylate and methacrylate esters, as well as blends of the homo- and copolymers of alpha-olefins with other types of thermoplastic polymers;

Polymers of styrene including polystyrene, poly(alphamethyl styrene) and poly(tertiary butyl styrene) and copolymers of styrene, alpha methyl styrene or tertiary butyl styrene with a minor proportion of one or more ethylenically unsaturated comonomers such, for example, as nitriles of ethylenically unsaturated carboxylic acids including acrylonitrile and methacrylonitrile; $C_1$–$C_{12}$ alkyl esters of acrylic and methacrylic acids such, for example, as methyl methacrylate and 2-ethylhexyl acrylate; and, graft copolymers of styrene, tertiary butyl styrene or alpha-methyl styrene with polybutadiene and other hydrocarbon elastomers;

Cellulosic resins including cellulose esters and mixed esters such, for example, as cellulose nitrate, cellulose acetate-butyrate, cellulose acetate-propionate and cellulose ethers such, for example, as ethyl cellulose;

Polyamide resins, i.e. the resins made by the condensation of di- or polyamines with di- or polybasic acids or by polymerization of lactams or amino acids. Typical polyamides include nylon 4 which is made from pyrrolidone; nylon 6 obtained by polycondensation of caprolactam; nylon 66 obtained by the condensation of hexamethylene diamine with adipic acid; nylon 610 obtained by the condensation of hexamethylenediamine with sebacic acid; nylon 7 which is a polymer of ethyl aminoheptanoate; nylon 9 made from 9-aminononanoic acid; and, nylon 11 made from 11-amino undecanoic acid;

Polycarbonate resins, i.e. the resins derived from the reaction between a difunctional alcohol or phenol, such as bisphenol A, and phosgene or an alkyl or aryl carbonate;

Polyacetal resins, i.e. the resins derived from the anionic polymerization of formaldehyde to obtain a linear molecule of the type $-O-CH_2-O-CH_2-O-CH_2-$;

Polyphenylene oxide resins made by the oxidative polymerization of 2,6-dimethylphenol in the presence of a copper amine complex catalyst;

Polysulfone resins, i.e. the resins containing an $SO_2$ linkage as derived from the reaction of sulfur dioxide with olefins such as 1-butene or, more preferably, by reaction of bisphenol A with 4,4'-dichlorodiphenyl sulfone;

The acrylate:styrene:acrylonitrile resins, commonly referred to as "ASA" resins, which comprise copolymers containing a major proportion of a $C_2-C_8$ alkyl acrylate ester elastomer upon which is grafted about 65-95%, by weight of the latter copolymer, of a 70-80:30-20 styrene:acrylonitrile copolymer; and, the Methacrylate:butadiene:styrene resins, commonly referred to as the "MBS" resins, which comprise a minor proportion of a methyl methacrylate:styrene:acrylonitrile terpolymer grafted and/or blended with either polybutadiene or a copolymer of butadiene and minor proportions of such comonomers as, for example, styrene and acrylonitrile.

In all cases, bis(2,3-dibromopropyl) phosphite will provide blends with polymeric substrates which are characterized by their outstanding fire retardancy and their ease of blending. As used in this disclosure, the term "fire retardant" or "flame retardant" is intended to refer to that particular property of a material which provides it with a degree of resistance to ignition and burning. Thus, a fire or flame retardant composition is one which has a low level of flammability and flame spread.

The actual blending of the bis-(2,3-dibromopropyl) phosphite with the selected polymeric substrate, i.e. with any one or more of the above described polymers, may be accomplished by means of any convenient procedure which will result in an intimate admixture of the bis(2,3-dibromopyl) phosphite, within the mass of the substrate polymer. Thus, it may be included in the reaction mixture used to cure or polymerize the polymer or it may be blended with a previously prepared polymer.

With respect to proportions, the amount of the bis(2,3-dibromopropyl) phosphite which may be admixed with a polymer substrate will depend, primarily, upon such factors as the particular polymer substrate which is being utilized, the degree of fire retardancy desired in the resulting blend, the specific physical properties which are sought as well as other technical and economic considerations known and understood by those skilled in the art. However, in order to attain a composition which will be self-extinguishing, it is generally desirable to introduce an effective concentration of the additive which will be sufficient to provide the resulting blend with at least about 1%, by weight, of phosphorus. Thus, depending upon the above described factors, the blends containing the novel compounds of this invention will contain from about 5 to 30%, by weight, of bis(2,3-dibromopropyl) phosphite.

The resulting blends may also contain stabilizers, plasticizers, fillers, pigments, dyes, opacifying agents, decorative additives such as reflective metal foils or flakes, and other imbedded solid objects such as fiber glass, textile fibers, asbestos, paper, and the like, provided that they do not detract from the flame retardancy of these compositions. In addition, the composition may contain other flame retardants such as antimony compounds, chlorinated paraffins, perchlorinated alicyclic compounds, bromine containing organic compounds, halogenated alkyl phosphates or phosphonates, alkyl acid phosphates, or small concentrations of phosphoric acid.

The novel compositions of this invention, comprising blends of any of the above described polymers with bis(2,3-dibromopropyl) phosphite, may be utilized in any of the coating, molding, adhesive, impregnation, laminating and foaming applications known to those skilled in the art wherein it is desired to provide fire retardancy to the resulting end product. These fire retardant blends may, therefore, be used as coatings, impregnants, fillers, laminants, adhesives, etc. for such substrates as wood; paper; metals; textiles based on either natural or synthetic fibers or blends thereof; synthetic polymer films such as those based upon polyolefins, regenerated cellulose, i.e. cellophane, polyvinyl chloride, polyesters and the like; leather; natural and synthetic rubber; fiberboard; and, synthetic plastics prepared by means of either addition or condensation polymerization techniques.

The following examples will further illustrate the embodiment of this invention. In these examples, all parts given are by weight unless otherwise noted.

EXAMPLE I

This example illustrates the preparation of bis(2,3-dibromopropyl) phosphite by means of a process involving the reaction between tris(2,3-dibromopropyl) phosphite and phosphorous acid.

The tris(2,3-dibromopropyl) phosphite intermediate is first prepared by introducing 45.8 gms. (0.33 moles) of $PCl_3$ into a solution of 218 gms. (1.0 mole) of 2,3-dibromopropanol dissolved in 200 ml. of benzene. The reaction is conducted under agitation, at a temperature of about 0°–5° C. while bubbling dry nitrogen through the solution in order to eliminate by-product HCl as it is formed. The addition of the $PCl_3$ is completed in one hour and stirring is then continued for an additional 2 hours while maintaining the temperature at 0°–5° C. and continuing the bubbling of nitrogen into the system. A water aspirator is then applied for 30 minutes whereupon the intermediate is recovered by stripping the solvent from the reaction product.

A total of 13.12 gms. (0.16 moles) of $H_3PO_3$ is admixed with the tris(2,3-dibromopropyl) phosphite intermediate resulting from the stripping of the solvent from the reaction product described hereinabove. The resulting mixture is stirred and heated for 6½ hours at 80° C. while under a nitrogen atmosphere. The reaction product is cooled to room temperature whereupon it is taken up in 200 ml. of methylene chloride and then washed with 400 ml. of a 5%, by weight, aqueous solution of $NaHCO_3$. The organic layer is then washed with 400 ml. of water whereupon it is separated, dried over anhydrous magnesium sulfate and finally the solvent is stripped. This procedure yields 228 gms., corresponding to an 86% yield of the bis(2,3-dibromopropyl) phosphite in the form of a clear white liquid whose refractive index $n_D^{24} = 1.5664$. The amount of P-H groups in this product is determined by means of nuclear magnetic resonance and indicates a purity of 80–85%.

| Analysis: | Observed | Theoretical |
|---|---|---|
| % P | 5.5 | 6.4 |
| % Br | 69.1 | 66.4 |

EXAMPLE II

This example illustrates the use of bis(2,3-dibromopropyl) phosphite in preparing a flame retardant polyester resin composition.

Rods whose dimensions are 13mm × 100mm are prepared by first intimately admixing 9.0 gms. of a styrenated polyester resin, as sold under the trademark "Koplac 1060-5" by the Koppers Co., Inc., 1.0 gm., i.e. 10% of the total weight of the mixture, of bis(2,3-dibromopropyl) phosphite, as prepared in Example I hereinabove, and 0.1 gms. of benzoyl peroxide. The resulting mixture is then cured in tube shaped molds for one hour at 100° C. and then for an additional 18 hours at 135°–140° C. Additional samples are prepared in which the concentration of the bis(2,3-dibromopropyl) phosphite is, respectively, 15% and 20% of the total weight of the resulting blend.

As controls for this experiment, identical rod shaped samples are prepared which, in one instance, are devoid of the bis(2,3-dibromopropyl) phosphite additive while another set of resin samples contain equivalent amounts, i.e. 10, 15 and 20% of tris(2,3-dibromopropyl) phosphate, which is a commercially utilized flame retardant additive, in place of the bis(2,3-dibromopropyl) phosphite.

The flame retardancy of these polyester resin samples is evaluated by means of the Limiting Oxygen Index (LOI) method as determined by means of ASTM D-2863; the latter procedure also being described by Fenimore and Martin in the November, 1966 issue of Modern Plastics. In brief, this procedure directly relates flame retardancy to a measurement of the minimum percentage concentration of oxygen in an oxygen:nitrogen mixture which permits the sample to burn; the LOI being calculated as follows:

$$LOI = \frac{[O_2]}{[O_2] + [N_2]} \times 100$$

Thus, a higher LOI is indicative of a higher degree of flame retardancy.

| | | \multicolumn{4}{c}{FLAME RETARDANCY OF POLYESTER RESIN SAMPLES} | | | |
|---|---|---|---|---|---|
| | | \multicolumn{4}{c}{LOI} | | | |
| Additive | Conc. of Additive (%) | 0 | 10 | 15 | 20 |
| Bis(2,3-dibromopropyl) phosphite | | 17.70 | 21.60 | 23.60 | 24.70 |
| Tris(2,3-dibromopropyl) phosphate | | 17.70 | 21.00 | 22.84 | 24.26 |

The above data reveal that bis(2,3-dibromopropyl) phosphite provides excellent results when used as a flame retardant additive for polyester resins; these results being better than those achieved with a commercially available phosphate additive.

EXAMPLE III

This example illustrates the use of bis(2,3-dibromopropyl) phosphite in preparing a flame retardant polymethyl methacrylate composition.

Rods whose dimensions are 13mm × 100mm are prepared by first intimately admixing 9 gms. of methyl methacrylate and 1 gm., i.e. 10% of the total weight of the mixture, of bis(2,3-dibromopropyl) phosphite, as prepared in Example I hereinabove. The resulting mixture is then cured, i.e. polymerized, in tube shaped molds for 16 hours at 60° C. in the presence of 0.5%, based on the weight of the methyl methacrylate, of azobisisobutyronitrile as a catalyst. Additional samples are prepared in which the concentration of the bis(2,3-dibromopropyl) phosphite is, respectively, 15% and 20% of the total weight of the resulting blend.

As controls for this experiment, identical rod shaped samples are prepared which, in one instance, are devoid of bis(2,3-dibromopropyl) phosphite while another set contain an equivalent amount of tris(2,3-dibromopropyl) phosphate, which is a commercially utilized flame retardant additive, in place of the bis(2,3-dibromopropyl) phosphite. The flame retardancy of these polymethyl methacrylate resin samples is evaluated by means of the Limiting Oxygen Index (LOI) method with the results of this evaluation being reported in the following table.

| | | \multicolumn{4}{c}{FLAME RETARDANCY OF POLYMETHYL METHACRYLATE RESIN SAMPLES} | | | |
|---|---|---|---|---|---|
| | | \multicolumn{4}{c}{LOI} | | | |
| Additive | Conc. of Additive (%) | 0 | 10 | 15 | 20 |
| Bis(2,3-dibromopropyl) phosphite | | 16.85 | 20.80 | 22.30 | 23.20 |
| Tris(2,3-dibromopropyl) phosphate | | 16.85 | 20.35 | — | — |

The above data reveal that bis(2,3-dibromopropyl) phosphite provides excellent results when used as a flame retardant additive for polymethyl methacrylate; these results being better than those achieved with a commercially available additive. Comparable results are obtained when bis(2,3-dibromopropyl) phosphite is incorporated into a flexible urethane foam as a flame retardant additive.

Variations may be made in proportions, procedures and materials without departing from the scope of this invention as defined in the following claims.

What is claimed is:

1. A process for the preparation of bis(2,3-dibromopropyl) phosphite, said process comprising reacting tris(2,3-dibromopropyl) phosphite with phosphorous acid at an elevated temperature and recovering the bis(2,3-dibromopropyl) phosphite thus produced.

2. The process of claim 1, wherein said reaction is conducted in an inert atmosphere.

3. A process as claimed in claim 1 wherein the reaction is carried out at a temperature of about 80° C. to 150° C.

4. A process as claimed in claim 1 wherein the phosphorus acid is reacted with double its concentration of tris(2,3-dibromopropyl)phosphite.

5. A process as claimed in claim 1 wherein the reaction is conducted over a period of 1 to 6 hours.

6. A process as claimed in claim 1 wherein the reaction is carried out in the presence of an inert gas.

7. A process as claimed in claim 6 wherein the inert gas is nitrogen.

* * * * *